(12) United States Patent
Miyazaki et al.

(10) Patent No.: US 7,734,006 B2
(45) Date of Patent: Jun. 8, 2010

(54) X-RAY CT APPARATUS

(75) Inventors: Osamu Miyazaki, Moriya (JP); Koichi Hirokawa, Kashiwa (JP); Hironori Ueki, Kokubunji (JP)

(73) Assignee: Hitachi Medical Corporation, Tokyo (JP)

( * ) Notice: Subject to any disclaimer, the term of this patent is extended or adjusted under 35 U.S.C. 154(b) by 16 days.

(21) Appl. No.: 11/887,875

(22) PCT Filed: Mar. 31, 2006

(86) PCT No.: PCT/JP2006/306880

§ 371 (c)(1),
(2), (4) Date: Jun. 17, 2008

(87) PCT Pub. No.: WO2006/106941

PCT Pub. Date: Oct. 12, 2006

(65) Prior Publication Data

US 2008/0240336 A1     Oct. 2, 2008

(30) Foreign Application Priority Data

Apr. 4, 2005     (JP)     ............................... 2005-107566

(51) Int. Cl.
*G01N 23/00*     (2006.01)

(52) U.S. Cl. ........................... 378/8; 378/101; 378/109; 378/111

(58) Field of Classification Search ............... 378/4, 378/8, 91, 95, 98, 98.2, 98.5, 101, 109–112, 378/114–117
See application file for complete search history.

(56) References Cited

U.S. PATENT DOCUMENTS 6,490,337 B1     12/2002     Nagaoka et al.

(Continued)

FOREIGN PATENT DOCUMENTS

EP     1393681 A1     3/2004

(Continued)

OTHER PUBLICATIONS

English translation of Mar. 6, 2008 PCT International Preliminary Report on Patentability in connection with counterpart PCT international application No. PCT/JP2006/306880.

(Continued)

*Primary Examiner*—Jurie Yun
(74) *Attorney, Agent, or Firm*—Cooper & Dunham LLP

(57) ABSTRACT

In the X-ray CT apparatus of the present invention, the setting device sets X-ray irradiation condition candidate by at least one combination of a tube current and tube voltage for power to be supplied to the X-ray source by the use of an X-ray absorption coefficient of said scanning subject site of the object, and the control device makes the display device selectably display each of the set X-ray irradiation condition candidates which is provided for a diagnosis of a requested tissue of the object, to take control such that a tomographic image of the object is taken according to the selected X-ray irradiation condition candidate. According to the X-ray CT apparatus of the present invention, it is possible to set a scanning condition in view of absorption or transmission of X-rays specific to and different among each tissue of an object.

13 Claims, 13 Drawing Sheets

U.S. PATENT DOCUMENTS

| | | |
|---|---|---|
| 2003/0016778 A1 | 1/2003 | Tachizaki et al. |
| 2004/0062341 A1 | 4/2004 | Popescu et al. |
| 2004/0086076 A1 | 5/2004 | Nagaoka et al. |
| 2005/0008115 A1 | 1/2005 | Tsukagoshi |

FOREIGN PATENT DOCUMENTS

| | | | |
|---|---|---|---|
| JP | 8-66389 | | 3/1996 |
| JP | 2001-8930 | | 1/2001 |
| JP | 2001-008930 | * | 1/2001 |
| JP | 2004-73865 | | 3/2004 |

OTHER PUBLICATIONS

English translation of Feb. 6, 2009 Chinese official action in connection with a counterpart Chinese patent application No. 200680010780.1.

English translation of Aug. 7, 2009 Chinese official action in connection with a counterpart Chinese patent application No. 200680010780.1.

Nov. 3, 2009 European search report in connection with a counterpart European patent application No. 06 73 0828.

* cited by examiner

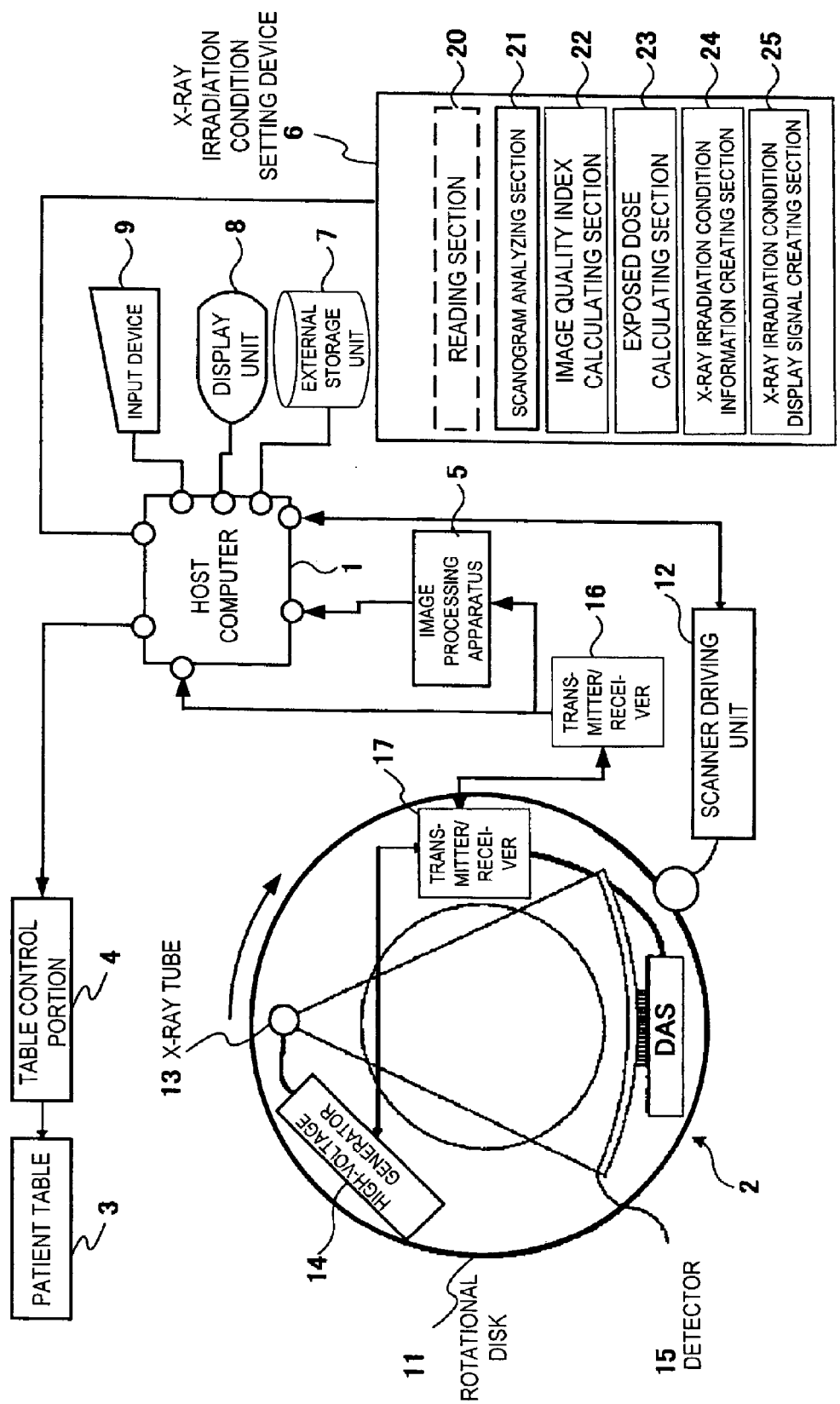

FIG.2

| | SCANNING PROTOCOL | TISSUE a/b | TISSUE b DENSITY | TISSUE b SIZE |
|---|---|---|---|---|
| 1 | HEAD PLAIN | WATER/BLOOD | 0.1 | 5[mm] |
| 2 | HEAD CTA | WATER/ CONTRAST AGENT | 0.01 | 0.625[mm] |
| 3 | LIVER THREE-PHASE | WATER/BLOOD | 0.1 | 5[mm] |
| 4 | LOWER EXTREMITY BLOOD VESSEL | WATER/ CONTRAST AGENT | 0.01 | 1.25[mm] |
| 5 | CHEST PLAIN | AIR/BLOOD | 0.5 | 0.625[mm] |
| 6 | CORONARY ANGIOGRAPHY | WATER/ CONTRAST AGENT | 0.1 | 0.625[mm] |
| 7 | BONE | WATER/BONE | 0.8 | 0.625[mm] |

FIG.3

ACQUIRING TRANSMISSION THICKNESS INFORMATION — S101

CALCULATING IMAGE QUALITY INDEX — S102

CALCULATING EXPOSED DOSE — S103

CREATING X-RAY IRRADIATION CONDITION INFORMATION — S104

DISPLAYING X-RAY IRRADIATION CONDITION INFORMATION — S105

SELECTING X-RAY IRRADIATION CONDITION — S106

SETTING X-RAY IRRADIATION CONDITION — S107

| X-RAY IRRADIATION CONDITION (TUBE CURRENT,TUBE VOLTAGE) | CNR | EXPOSED DOSE | CNR/EXPOSED DOSE |
|---|---|---|---|
| X-RAY IRRADIATION CONDITION A (...mA・...Kv) | ○○(LEVEL1) | ○○(LEVEL○○) | ○○(LEVEL○○) |
| X-RAY IRRADIATION CONDITION B (...mA・...Kv) | ○○(LEVEL1) | △△(LEVEL△△) | △△(LEVEL△△) |
| X-RAY IRRADIATION CONDITION C (...mA・...Kv) | △△(LEVEL2) | ××(LEVEL××) | ××(LEVEL××) |
| ......... | ......... | ......... | ......... |
| ......... | ......... | ......... | ......... |
| ......... | ......... | ......... | ......... |
| ......... | ......... | ......... | ......... |

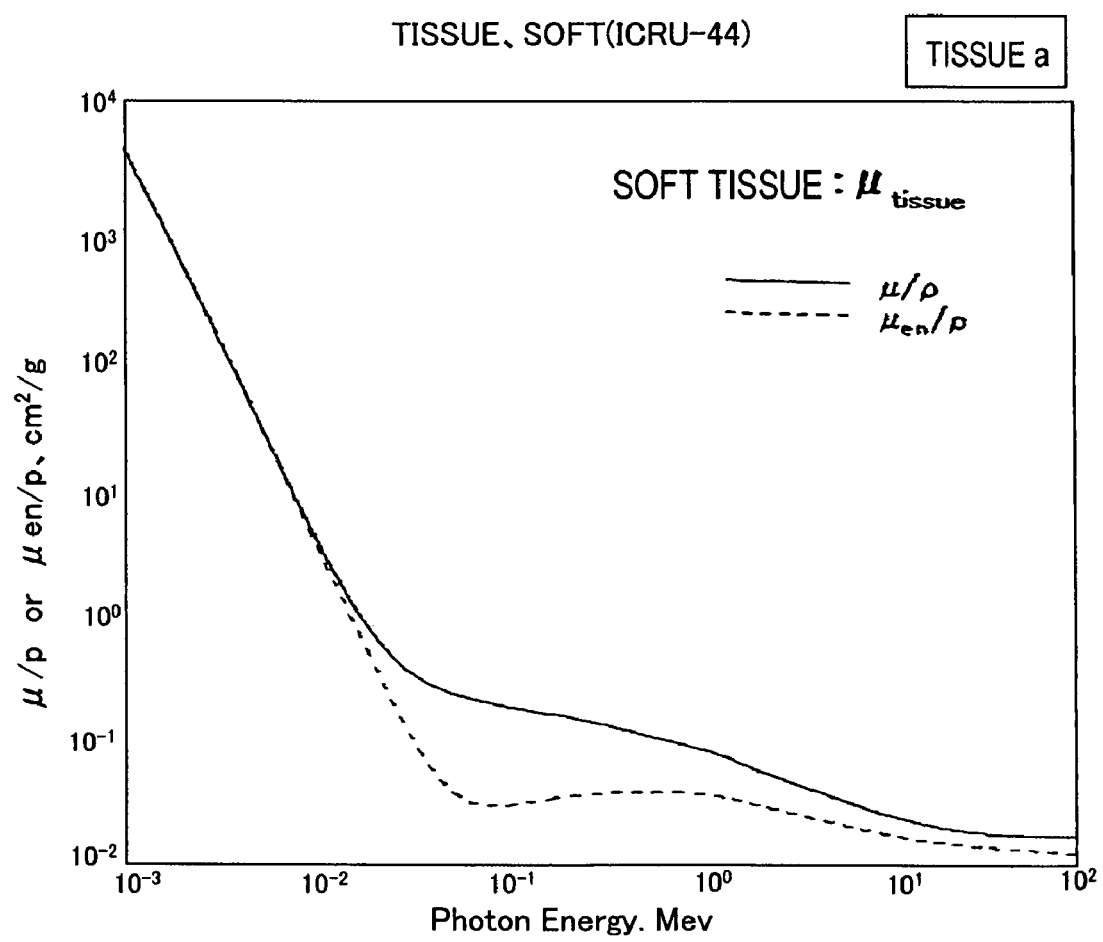

FIG. 11

| CNR | SNR | EXPOSED DOSE | TRANSMISSION THICKNESS | X-RAY IRRADIATION CONDITION (TUBE CURRENT, TUBE VOLTAGE) | SCANNING PROTOCOL |
|---|---|---|---|---|---|
| ○○(LEVEL 1) | ○○(LEVEL 1) | ○○(LEVEL 1) | xx | X-RAY IRRADIATION CONDITION A (...mA・...kV) | HEAD PLAIN |
| ○○(LEVEL 1) | △△(LEVEL 2) | ○○(LEVEL 1) | yy | X-RAY IRRADIATION CONDITION B (...mA・...kV) | HEAD PLAIN |
| △△(LEVEL 2) | △△(LEVEL 2) | △△(LEVEL 2) | zz | X-RAY IRRADIATION CONDITION C (...mA・...kV) | HEAD PLAIN |
| ⋮ | ⋮ | ⋮ | ⋮ | ⋮ | ⋮ |
| ○○(LEVEL 1) | △△(LEVEL 2) | △△(LEVEL 2) | xx | X-RAY IRRADIATION CONDITION A (...mA・...kV) | HEAD CTA |
| ○○(LEVEL 1) | △△(LEVEL 2) | △△(LEVEL 2) | yy | X-RAY IRRADIATION CONDITION B (...mA・...kV) | HEAD CTA |
| △△(LEVEL 2) | △△(LEVEL 2) | △△(LEVEL 2) | zz | X-RAY IRRADIATION CONDITION C (...mA・...kV) | HEAD CTA |
| ⋮ | ⋮ | ⋮ | ⋮ | ⋮ | ⋮ |

| USER ID | | SCANNING PROTOCOL | TISSUE a/b | TISSUE b DENSITY | TISSUE b SIZE |
|---|---|---|---|---|---|
| 001 | 1 | HEAD PLAIN | WATER/BLOOD | 0.1 | 3 [mm] |
| 001 | 2 | HEAD CTA | WATER/ CONTRAST AGENT | 0.01 | 0.625[mm] |
| 001 | 3 | LIVER THREE-PHASE | WATER/BLOOD | 0.1 | 5[mm] |
| 001 | 4 | LOWER EXTREMITY BLOOD VESSEL | WATER/ CONTRAST AGENT | 0.01 | 1.25[mm] |
| 001 | 5 | CHEST PLAIN | AIR/BLOOD | 0.5 | 0.625[mm] |
| 001 | 6 | CORONARY ANGIOGRAPHY | WATER/ CONTRAST AGENT | 0.1 | 0.625[mm] |
| 001 | 7 | BONE | WATER/BONE | 0.8 | 0.625[mm] |

X-RAY CT APPARATUS

TECHNICAL FIELD

The present invention relates to an X-ray CT apparatus, and particularly to an X-ray CT apparatus which allows selective setting of an X-ray irradiation condition according to a tissue of an object or the like, and allows reduction in exposed dose of the object to the minimum while maintaining an image quality necessary for a diagnosis according to the setting.

The present application is an application associated with claim to priority on the basis of patent application Ser. No. 2005-107566 based upon the Japanese Patent Law, as well as an application which benefits by reference for enjoying a benefit of Patent Application No. 2005-107566.

BACKGROUND ART

Techniques for reducing an exposed dose of an object while attempting to improve an image quality have conventionally been developed. For example, in Patent Document 1, a beam hardening error of obtained projection data is subjected to a correction process according to a scanning method, and a plurality of irradiator current values are created, which are then applied to a scanning system according to a scanning subject. It is thereby possible to reduce a dose received by individual objects and also enhance a dose efficiency regardless of sizes of the objects, while holding a low noise level to an allowable extent and favorable CNR.

Patent Document 1: Japanese Patent Laid-Open No. 2004-73865

Image quality of an X-ray CT image is largely involved in visual inspection, by a doctor, of a seat of disease in a tissue of an object or the like. To obtain better image quality, scanning condition can be set in view of absorption or transmission of X-rays specific to and different among each tissue of an object. However, in Patent Document 1, consideration is not given to setting of a scanning condition in view of absorption or transmission of X-rays specific to and different among each tissue of an object.

SUMMARY

In an aspect of this disclosure, there is provided an X-ray CT apparatus capable of setting a scanning condition in view of absorption or transmission of X-rays specific to and different among each tissue of an object.

An X-ray CT apparatus, according to an exemplary embodiment of the disclosure, comprises: an X-ray source which irradiates X-rays; an X-ray detector which is arranged oppositely to the X-ray source and detects the irradiated X-rays; a scanner having a rotary disk which rotatably supports the X-ray source and X-ray detector and a power source of the rotary disk; an image processing device which makes the scanner rotate in a state where an object is inserted in between the X-ray source and the X-ray detector to irradiate the object with X-rays from directions at a plurality of angles, and makes the X-ray detector detect X-rays transmitted through the object in directions at a plurality of angles as projection data, to reconstruct a tomographic image of the object by the use of the projection data in the directions at the plurality of angles; a display device which displays the reconstructed tomographic image; a setting device which sets an X-ray irradiation condition candidate by at least one combination of a tube current and a tube voltage for power to be supplied to the X-ray source by the use of a transmission thickness of a scanning subject site of the object; and a control device which supplies the with an X-ray irradiation condition corresponding to the set X-ray irradiation condition candidate, to perform scanning, and in the X-ray CT apparatus, the setting device sets an X-ray irradiation condition candidate by at least one combination of a tube current and tube voltage for power to be supplied to the X-ray source by the use of an X-ray absorption coefficient of the scanning subject site of the object, and the control device makes the display device selectably display each of the set X-ray irradiation condition candidates which is provided for a diagnosis of a requested tissue of the object, to take control such that a tomographic image of the object is taken according to the selected X-ray irradiation condition candidate.

According to the above-mentioned X-ray CT apparatus, it is possible to set a scanning condition in view of absorption or transmission of X-rays specific to and different among each tissue of an object.

BRIEF DESCRIPTION OF THE DRAWINGS

FIG. 1 is a view showing a patternized configuration of an X-ray CT apparatus according to one embodiment;

FIG. 2 is a view showing a configuration of a scanning protocol/attenuation model table;

FIG. 3 is a view showing a flow of an X-ray irradiation condition setting process;

FIG. 6D is a view showing an example of a specification data regarding energy of X-rays and an absorption coefficient of a soft tissue;

FIG. 11 is a view schematically showing a correlation table for use in a second embodiment;

DESCRIPTION OF SYMBOLS

Figures 4, 5:
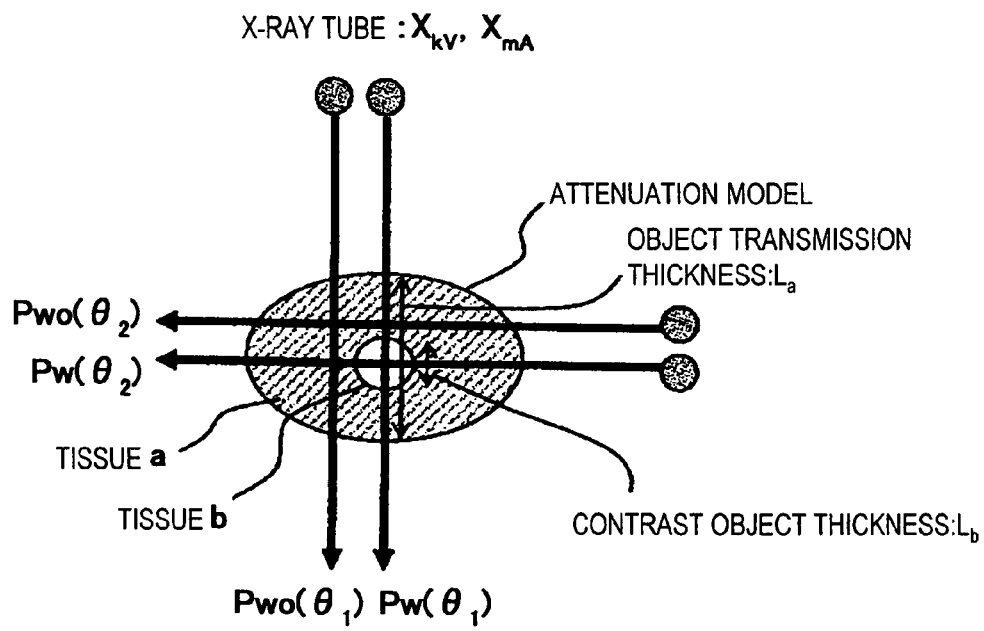
FIG. 4 is a view showing a simplified attenuation model.
FIG. 5 is a view showing an example of a correlation table constituting X-ray irradiation condition information.

6 X-ray irradiation condition setting device
22 Image quality index calculating section
23 Exposed dose calculating section
24 X-ray irradiation condition information creating section

BEST MODE FOR CARRYING OUT THE INVENTION

First Embodiment

In a first embodiment, when a scanning protocol such as a site desired to be diagnosed and the presence or absence of a contrast agent is designated, an image quality index, an exposed dose and the like regarding at least one combination of a tube current and tube voltage which is corresponded to this scanning protocol are calculated and displayed. The user then looks at the displayed results and selects a tube current and a tube voltage to be actually used for scanning.

In the following, embodiments of the present invention are described. FIG. 1 shows a patternized configuration of an X-ray CT apparatus according to one embodiment. The X-ray CT apparatus of the present embodiment comprises the following components. A host computer 1 is an overall control section for control over a system. On a rotational scanning structure 2, an X-ray irradiation system such as an X-ray tube 13 and an X-ray detection system such as a detector 15 are mounted, and the rotational scanning structure 2 rotates for scanning during scanning. A patient table 3 is a bed on which an object is set. A table control portion 4 controls an operation of the patient table 3 (ascent and descent of the object, etc. in the longitudinal direction), and an image processing apparatus 5 performs a variety of image processing such as a pre-process or a reconstruction process. The X-ray irradiation condition setting device 6 comprises the following components. The host computer 1 is connected with an external storage unit 7 as data storage device, and also connected with a display unit 8 and an input device 9. It should be noted that the patient table 3 is arranged in a circular space portion in the rotational scanning structure 2, but in FIG. 1, the patient table 3 has been set aside for simplification.

The rotational scanning structure (scanner) 2 has a rotary disk 11 and a scanner driving unit 12 that rotationally drives the rotary disk 11. The scanner driving unit 12 rotates the rotary disk 11 according to a designation from the host computer 1, and at a scanning preparation stage, the scanner driving unit 12 notifies the host computer 1 of completion of preparation at the time when a rotational speed of the rotary disk 11 becomes a predetermined one. The following components are mounted on the rotary disk 11. The X-ray tube 13 is an X-ray source. A high-voltage generator 14 is a power source for generating a voltage and a current for the X-ray tube 13. The detector 15 detects X-rays irradiated from the X-ray tube 13. A transmitter/receiver 17 transmits and receives data to and from a transmitter/receiver 16 provided in a static system (the host computer 1 and the image processing unit 5).

The X-ray tube 13 irradiates X-rays, which is obtained on an X-ray irradiation condition set in a manner as described later, toward the detector 15 during scanning. The detector 15 detects the X-rays having been transmitted through the object, converts the detected X-rays into an electric signal, and then acquires projection data as digital data in a measurement circuit. The projection data is subjected to a variety of processes in the image processing apparatus 5, including a pre-process, a filter process and a back projection process, and reconstructed as a tomographic image. The reconstructed image (tomographic image) is displayed on the display unit 8 to be provided to an image reading person as an image for a diagnosis.

The X-ray irradiation condition setting device 6 is configured as a computer program, and a function of this X-ray irradiation condition setting device 6 is described later.

In controlling of the patient table 3 by the table control portion 4, for example in the case of spiral scanning, the patient table 3 is previously shifted to a position in view of an accelerated time of the patient table 3. Subsequently, the patient table 3 starts shifting from its shifted position, and the table control portion 4 controls the patient table 3 such that the speed of the patient table 3 becomes constant before the patient table 3 reaches a position (X-ray exposure start position) where the object on the patient table 3 starts being irradiated with X-rays.

In the following, a flow of a process in scanning performed by the X-ray CT apparatus of the present embodiment is described. In a scanning mode, first, a scanning protocol is set. Examples of the scanning protocol may include head plain, head CTA (CT Angiography), chest general, chest three-phase scanning, and lower extremity angiography. These scanning protocols are converted into data in a table form as an example shown in FIG. 2, for example, and previously registered into scanning protocol/attenuation model database set in the external storage unit 7. Therefore, setting of a scanning protocol is made by selecting a necessary one from scanning protocol/attenuation model database.

Next, the scanning protocol is shifted to scanogram imaging. The scanogram imaging is aimed at acquiring an image for positioning and information such as a size, namely a transmission thickness, of an object. The scanogram imaging can be performed in the up and down direction and the right and left direction. Although information about a transmission thickness (thickness and width) of an object can normally be obtained by imaging in either the up and down direction or the right and left direction, imaging may be performed in the both directions according to the need.

Subsequently, a scanning condition, a reconstruction condition and the like are set along with setting of a scanning range of a tomographic image by the use of a scanogram. As the scanning conditions, an X-ray irradiation condition, a slice thickness, a table forwarding (spiral pitch) and the like are set.

The X-ray irradiation condition is carried out by the use of the X-ray irradiation condition setting device 6. FIG. 3 shows a flow of an X-ray irradiation condition setting process performed by the X-ray irradiation condition setting device 6. First, transmission thickness information of an object is acquired (Step S101). This process of the first embodiment is performed by skipping a reading section 20 surrounded by a dotted line and analyzing a scanogram by a scanogram analyzing section 21. The reading section 20 is used in a second embodiment. In the scanogram analysis, the user needs to designate a position of an analysis object. The analysis object position is a position in the axial direction of the object, namely in the z-direction, and corresponds to a slice position (scanning subject site) in taking tomographic image. The designation can be made by operation of a marker or the like on a screen displaying a scanogram or previous definition in the scanning protocol.

Subsequently, an image quality index calculating section 22 calculates an image quality index (Step S102). The image quality index is calculated by the use of an attenuation model. The attenuation model is obtained by modeling a tissue configuration in an image quality index calculating position, namely an attenuation structure of X-rays, as a simplified example shown in FIG. 4. The image quality index calculating position is a slice position in tomographic image taking, and thus is also an analysis object position in scanogram analysis. The example of FIG. 4 is a model made up of a tissue a and a tissue b. Such an attenuation model is prepared for each scanning protocol. In the present embodiment, as shown in FIG. 2, the attenuation model is previously formed into data form corresponded to a scanning protocol by the use of the scanning protocol/attenuation model table, and then previously registered into the scanning protocol/attenuation model database.

The image quality index calculating section 22 reads an attenuation model corresponding to the scanning protocol set as described above at the start of the image quality index calculation process. The image quality index calculating section 22 then applies the X-ray irradiation condition to this attenuation model and transmission thickness information of the object obtained by the above scanogram analysis, to calculate an image quality index. Here, the image quality index is an index regarding an image quality (image readability) of an image obtained by scanning. SNR (signal/noise ratio), CNR (contrast/noise ratio) or the like can be used for such an image quality index. As described above, contrast of a diagnosis object tissue with a background makes up a large portion of the image readability of an image by the X-ray CT apparatus. Namely, the X-ray CT apparatus has a characteristic that image reading of a diagnosis object tissue is possible when the contrast is large enough with respect to the image noise. By taking advantage of such a characteristic, it is possible to set a further appropriate X-ray irradiation condition. From this perspective, it is more preferable to use CNR for an image quality index, and CNR is used in the present embodiment.

The image quality index is obtained for each of a plurality of X-ray irradiation condition candidates. The X-ray irradiation condition candidates are previously registered in the X-ray irradiation condition database set in the external storage unit 7. For example, six kinds of tube currents: 100 mA, 150 mA, 200 mA, 250 mA, 300 mA and 350 mA, and five kinds of tube voltages: 80 kV, 100 kV, 120 kV, 130 kV and 140 kV are set, and a plurality of X-ray irradiation condition candidates as combinations of these tube currents and tube voltages are previously prepared.

Next, an exposed dose calculating section 23 calculates an exposed dose (Step S103). The exposed dose is calculated by applying the X-ray irradiation condition to the attenuation model and the transmission thickness information of the specific in the same manner as the calculation of the image quality index, and obtained for each of the plurality of X-ray irradiation condition candidates.

When the image quality index and the exposed dose for each of the plurality of kinds of X-ray irradiation condition candidates are obtained in the above manner, X-ray irradiation condition information is then created by an X-ray irradiation condition information creating section 24 by the use of the plurality of X-ray irradiation condition candidates, and the image quality indexes and the exposed doses which correspond to those candidates (Step S104). In the present embodiment, the X-ray irradiation condition information is created in the form of a correlation table as an example shown in FIG. 5. In the example of FIG. 5, a tube current and a tube voltage are shown in each of the plurality of X-ray irradiation condition candidates which are referred to as X-ray irradiation conditions A, B, C, . . . , and an image quality index (CNR) with an image quality level written in addition, an exposed dose with an exposed dose level written in addition, and a value obtained by dividing CNR by the exposed dose (CNR/exposed dose) are corresponded to each of the X-ray irradiation conditions. (CNR/exposed dose) shows that the larger the value, the larger CNR with respect to the exposed dose per unit, namely the better image quality. Although each of the X-ray irradiation conditions is shown as correlated with CNR, the exposed dose and (CNR/exposed dose) in FIG. 5, the X-ray irradiation condition may be displayed as correlated with any one of these three. Further, the X-ray irradiation condition may be displayed as correlated with an arbitrary combination among the three. Although the X-ray irradiation conditions are arranged in order of decreasing image quality level in the example of FIG. 5, the arrangement may be made in order of increasing exposed dose or in order of decreasing (CNR/exposed dose). Moreover, the user may be made to input a condition for determining an arrangement order, and the conditions may be arranged and displayed in order of adaptability to this inputted condition.

The X-ray irradiation condition information according to this correlation table is displayed on the display unit in Step S105, and in subsequent Step S106, the radiographer selects an X-ray irradiation condition with reference to the correlation table displayed on the display unit. In such selection, the radiographer considers a variety of requirements such as an image quality and an operating condition of the X-ray CT apparatus according to a diagnosis purpose, and with all those considered, the radiographer selects one X-ray irradiation condition from the correlation table. When the X-ray irradiation condition is selected by the radiographer, with such a condition taken as a final X-ray irradiation condition, X-ray irradiation condition information is created by the X-ray irradiation condition information creating section 24, which is A-D converted by an X-ray irradiation condition display signal creating section 25, and displayed on the display unit 8 via the host computer 1 (Step S107).

Here, the tube current is controlled while it is taken into consideration that an average transmission length of X-rays in the object varies depending upon an irradiation angle of X-rays against the object. Namely, the control is taken such that the tube current is increased in the case of a large irradiation angle at which the transmission length is large and the tube current is decreased in the case of a small irradiation angle at which the transmission length is small, so as to keep an output of the detector at a constant level. The transmission thickness information acquired by the above-mentioned scanogram analysis is applied to the transmission length as a parameter in this case. Further, axes in the control are those in the axial direction Z and the rotational direction (view angle) Θ, and the tube current is modulated with respect to the parameters. The tube current in the X-ray irradiation condition set by the X-ray irradiation condition setting device 6 is used as a reference tube current in the modulation. For example, in the case of taking the reference tube current as the maximum value in the modulation control, when the maximum value is M and an amplitude modulation pattern is P(Z, Θ), the tube current I is expressed by the following expression (1):

[Formula 1]

$$I(Z,\Theta) = M \times P(Z,\Theta) \tag{1}$$

As thus described, the X-ray irradiation condition information created by obtaining an image quality index and an exposed dose for each of a plurality of X-ray irradiation condition candidates is presented to radiographer so as to allow the radiographer to set an X-ray irradiation condition based upon this X-ray irradiation condition information, thereby making it possible to set an X-ray irradiation condition based mainly upon the relation between the exposed dose and the image quality, with other requirements also appropriately considered, so as to set a more appropriate X-ray irradiation condition.

In the following, calculation of CNR to be used as an image quality index is described. When irradiated X-rays are I0, and an integral value of an absorption coefficient on a transmission path is "$\mu(E) \times L$", transmitted X-rays I are expressed by a Formula (2):

[Formula 2]

$$I = \int I_0(E) \exp(-\mu(E) \times L) dE \quad (2)$$

Further, data P used for reconstruction takes a ratio to the irradiated X-rays, and is expressed by a Formula (3):

[Formula 3]

$$P = -\log(I/I_0(E)) \quad (3)$$

Here, assuming the attenuation model made up of the tissues a and b as in the example of FIG. 4, data Pw including the tissue b as a diagnosis object and Pw0 not including the tissue b are calculated by expressions (4) and (5), respectively, and a contrast C between the tissue a and the tissue b is calculated by an expression (6):

[Formula 4]

$$P_w = -\log \left[ \int I_0(E) \exp(\mu_a(E)d_a + \mu_b(E)d_b) dE / \int I_0(E) dE \right] \quad (4)$$

$$P_{w0} = -\log \left[ \int I_0(E) \exp(\mu_a(E)(d_a + d_b)) dE / \int I_0(E) dE \right] \quad (5)$$

$$C = P_w / P_{w0} \quad (6)$$

Figure 6A:
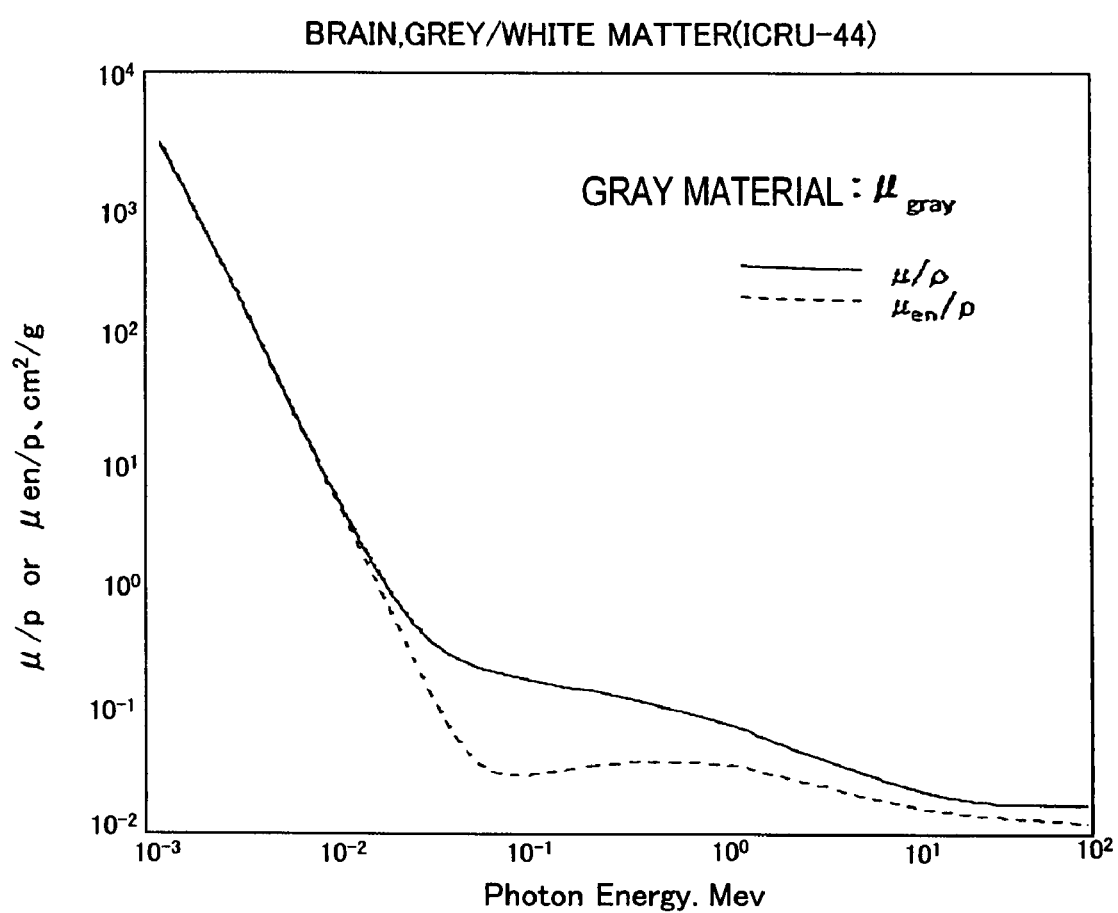
FIG. 6A is a view showing an example of specification data regarding energy of X-rays and an absorption coefficient of a grey matter.
Figure 6B:
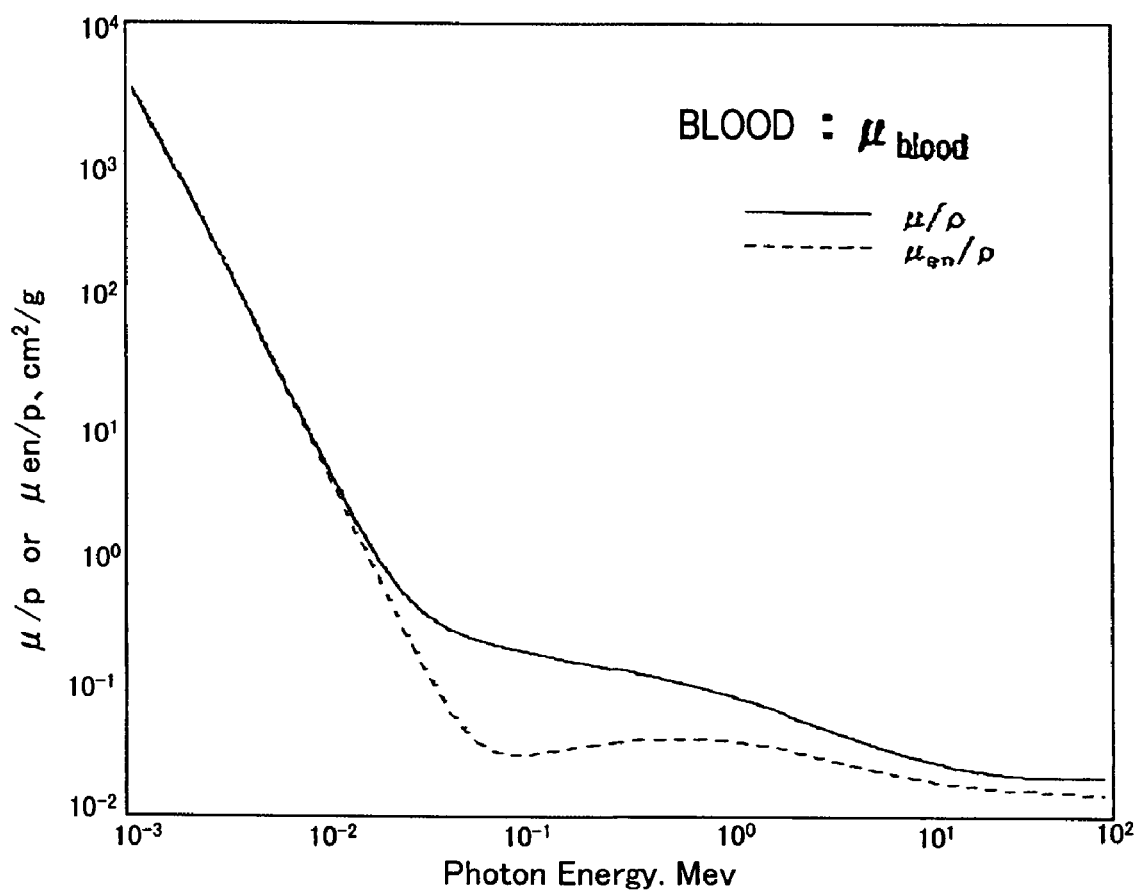
FIG. 6B is a view showing an example of a specification data regarding energy of X-rays and an absorption coefficient of blood.
Figure 6C:
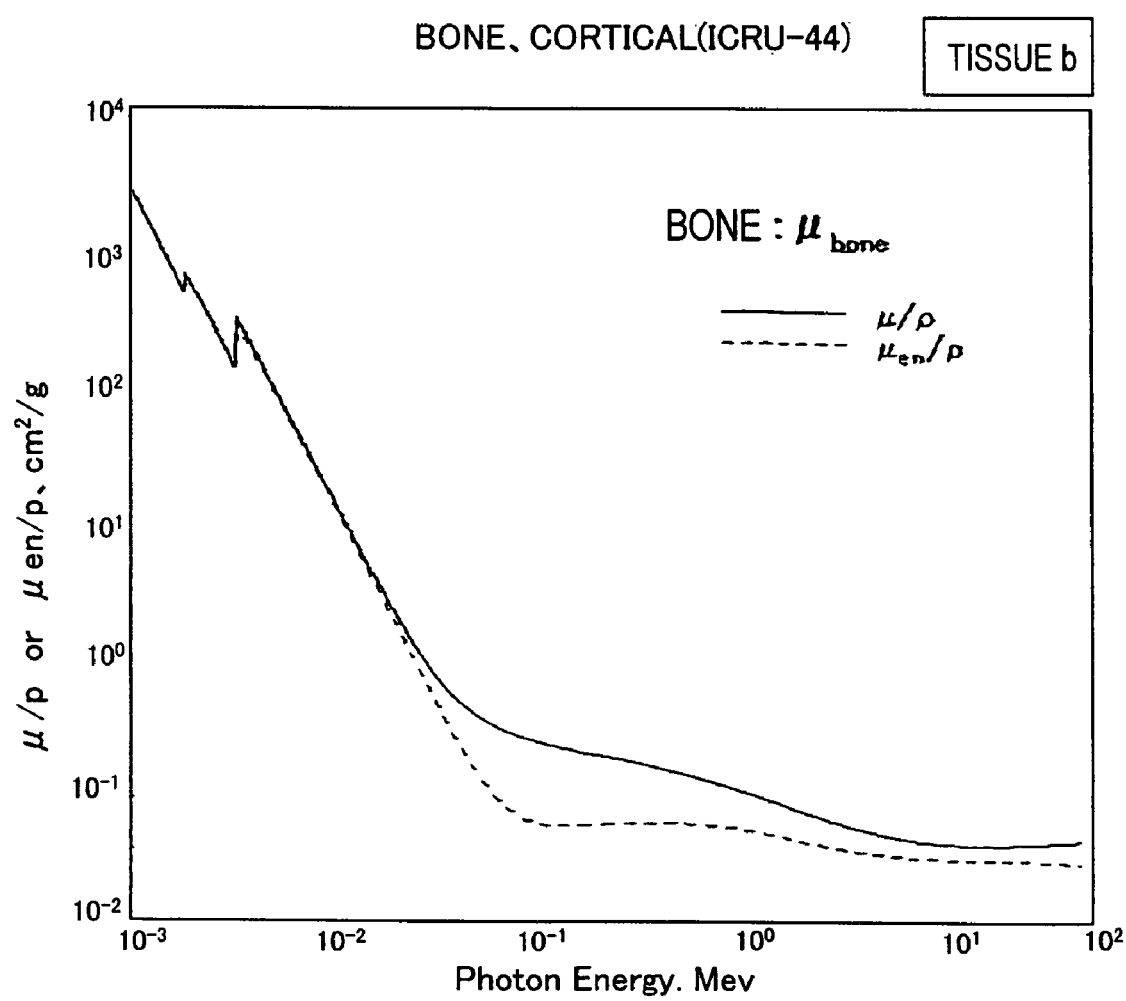
FIG. 6C is a view showing an example of a specification data regarding energy of X-rays and an absorption coefficient of a bone.

Here, the transmission length of Pw and the transmission length of Pw0 are "da+db" and thus equivalent. Further, the tissues a and b are, for example, water and a contrasted blood vessel, and defined for each of the foregoing attenuation models. For example, characteristic data $\mu(E)$ regarding X-ray energy and an absorption coefficient as shown in FIGS. 6A and 6B are prepared. $\mu/p$ indicates a value of the mass attenuation coefficient, and $\mu en/p$ indicates a value of the mass energy-absorption coefficient.

With the contrast C obtained in the above manner, when an image noise is Nw0 and the attenuation model is circular, CNR is expressed by an expression (7):

[Formula 5]

$$CNR = C/N_{w0} \quad (7)$$

Here, when the attenuation model is oval as in the example of FIG. 4, it is necessary in a strict sense to obtain contrasts and image noise in directions at a variety of angles and take average values, but in the simplest manner, as shown in FIG. 4, approximated values may be obtained only by projections Pw($\theta$1), Pw0($\theta$1) and Pw($\theta$2), Pw0($\theta$2) from two directions.

Figure 7:
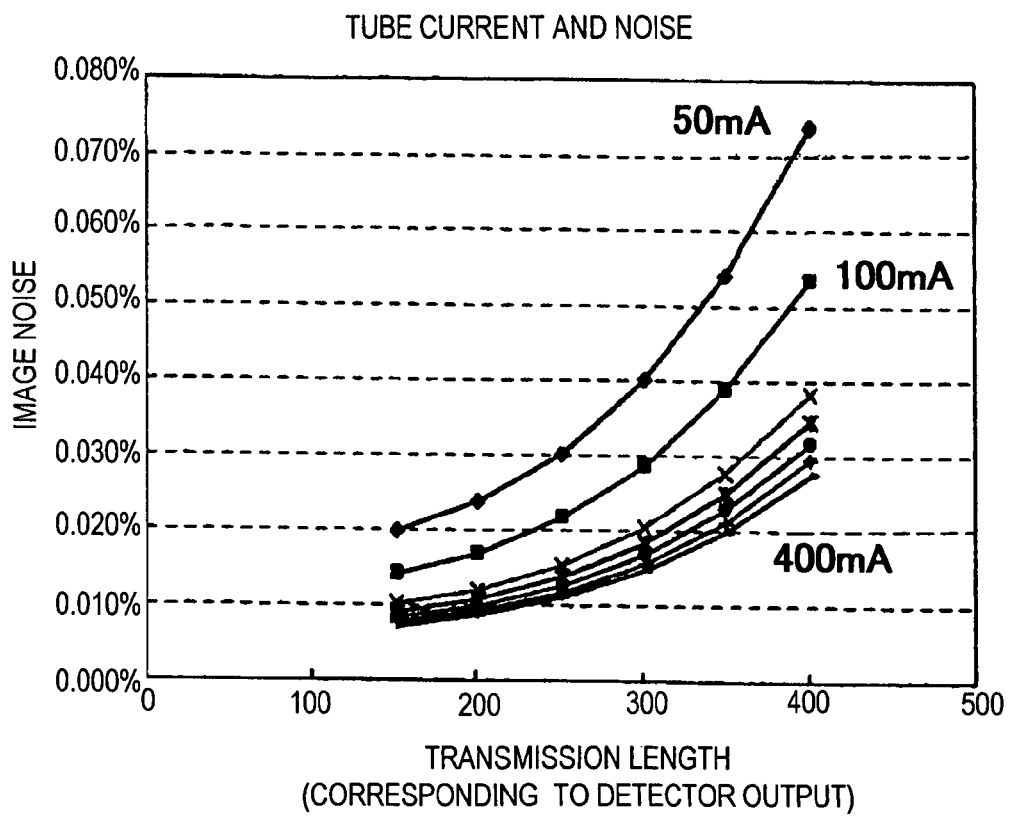
FIG. 7 is a view showing an example of data applicable to estimation of image noise.

Although the image noise Nw0 can also be estimated by calculation from a water equivalent thickness as the transmission thickness acquired by scanogram analysis and a scanning condition, the image noise Nw0 may be obtained by obtaining characteristics as shown in FIG. 7 by an examination and previously preparing a table of those characteristics.

Figure 8:
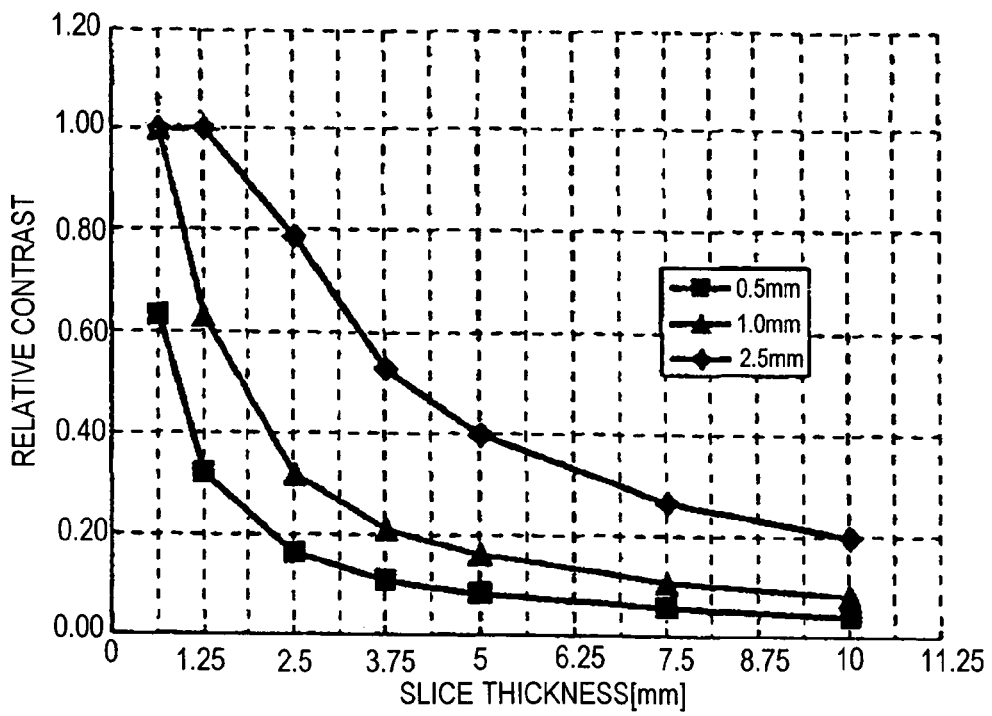
FIG. 8 is a view showing an example of a partial volume effect.

FIG. 8 shows an influence of a known partial volume effect, indicating that a contrast relatively decreases with increase in slice thickness. A system may also be formed where a decrease in contrast due to the partial volume effect as described above is considered in proportion to the size of the tissue b as the diagnosis object in FIG. 4, and according to such a system, calculation accuracy of CNR can be further increased.

Further, in the scanning protocol/attenuation model table of the example shown in FIG. 2, density information of the tissue b as the diagnosis object is registered along with size information of the tissue b. A system may also be formed where such density information is utilized, and according to such a system, calculation of CNR can be made flexible. For example in the case of conducting a non-contrast CT examination in diagnosis of cerebral infarction or the like, it is defined that what is wished to be detected is a slight change in blood capillary level. Further, when a seat of disease on the order of 5 mm is wished to be caught, since all of the 5 mm length is not that of the blood capillary, a ratio of a capillary bed contained in a 5 mm brain tissue can be defined as a density. Further, in the case of a contrast examination, since a contrast effect changes depending upon a concentration of iodine in a contrast agent to be used, it is possible to handle a variety of types of contrast agents in such a manner that only an absorption coefficient of iodine is stored and the tissue density is changed according to the concentration of iodine in the contrast agent to be used. Further, in the case of chest scanning, with branch structure close to the thinnest pleura being a blood capillary, scanning can be performed by making contrast between blood and air, and the density may be set higher than that of the blood capillary.

Although the exposed dose calculating section 23 is provided in the X-ray irradiation condition setting device 6 according to the present embodiment, the exposed dose calculating section 23 is not necessarily provided. In this case, Step S103 is omitted in FIG. 3. Further, in Steps S104 and S105, the exposed dose is not considered and X-ray irradiation condition information based upon the image quality index is created and displayed.

Figures 9, 10:
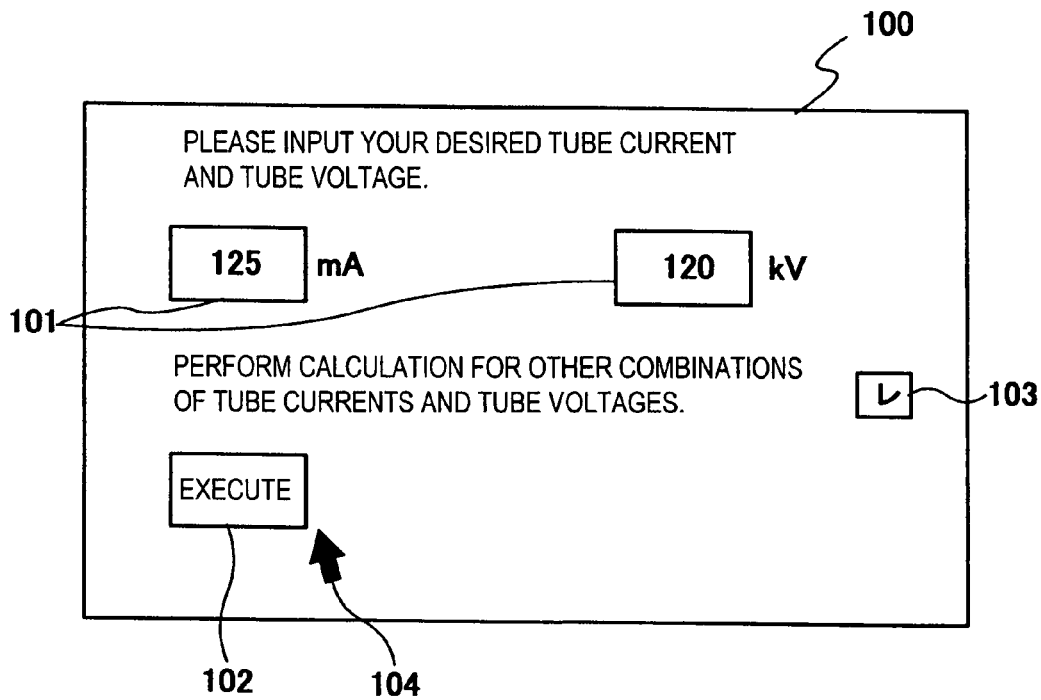
FIG. 9 is a view showing an example of an input screen for a tube current and a tube voltage.
FIG. 10 is a view showing an example of a result display screen.

Further, although the scanning protocol is designated in the present embodiment, a tube current/tube voltage input screen 100 shown in FIG. 9 may be displayed and a tube current and a tube voltage desired by the user may be inputted. The tube current/tube voltage input screen 100 is provided with an input field 101 of a tube current and a tube voltage, an execution button 102 for executing a process for calculating an image quality index and/or an exposed dose, and a check box 103 for selecting whether or not to perform calculation for other combinations of tube currents and tube voltages. When the user inputs a tube current and a tube voltage into the input field 101, places a mouse cursor 104 on the execution button 102 and clicks it, the image quality index calculating section 22 calculates an image quality index based upon the inputted tube current and tube voltage. Similarly, the exposed dose calculating section 23 calculates an exposed dose based upon the inputted tube current and tube voltage. The X-ray irradiation condition information creating section creates X-ray irradiation condition information based on the calculated tube current and tube voltage. The created result is displayed on the display unit 8.

When a check has been inputted in the check box 103, an image quality index and an exposed dose are calculated also for each of combinations of tube currents and tube voltages previously registered in the X-ray irradiation condition database set in the external storage unit 7.

FIG. 10 is an example of a result display screen when a check has been inputted in the check box 103. On a result display screen 110, a table is displayed where X-ray irradiation condition information with respect to the inputted tube current and tube voltage, the image quality index (CNR), the exposed dose and (CNR/exposed dose) of the X-ray irradiation condition candidate previously stored are mutually correlated. A row 112 displaying a result regarding the inputted tube current and tube voltage is displayed with its displaying color changed or an arrow 113 added thereto so as to facilitate distinction from other X-ray irradiation condition candidates. This allows estimation by comparing the X-ray irradiation condition by combination of the inputted tube current and tube voltage with the X-ray irradiation condition candidates.

Second Embodiment

In a second embodiment, when at least one of an image quality index and an exposed dose which are desired by the user, combinations of tube currents and tube voltages that match the inputted condition are displayed. The user selects a tube current and a tube voltage to be used for actual scanning among those displayed.

FIG. 1 is a block diagram showing a configuration of the X-ray irradiation condition setting section 6 according to the present embodiment. In addition to the configuration of the X-ray irradiation condition setting section 6 according to the first embodiment, the X-ray irradiation condition setting section 6 includes the reading section 20 for reading an X-ray irradiation condition candidate and a scanning protocol, which correspond to the inputted image quality index and/or an exposed dose, from a later-described correlation table of the CNR, exposed dose, transmission thickness, X-ray irradiation condition and scanning protocol in FIG. 11.

Further, in the external storage unit 7, the correlation table of the CNR, exposed dose, transmission thickness, X-ray irradiation condition and scanning protocol in FIG. 11 is stored. The correlation table of FIG. 11 is created such that the image quality index calculating section 22 and the exposed dose calculating section 23 in the first embodiment previously calculate an image quality index and an exposed dose in a case where a tube current, a tube voltage and an object transmission amount in some scanning protocol are determined and the X-ray irradiation condition information creating section 24 creates the table based upon the calculation and registered it in the external storage unit 7. Although the image quality index calculating section 22, the exposed dose calculating section 23 and the X-ray irradiation condition information creating section 24 function in the case of creating or updating the correlation table of FIG. 11, the image quality index calculating section 22, the exposed dose calculating section 23 and the X-ray irradiation condition information creating section 24 are not essential components in the case of previously creating the correlation table of FIG. 11 by another X-ray CT apparatus or a simulator apparatus and taking the created correlation table into the external storage unit 7. The item of (CNR/exposed dose) may be added to FIG. 11.

Figure 12:
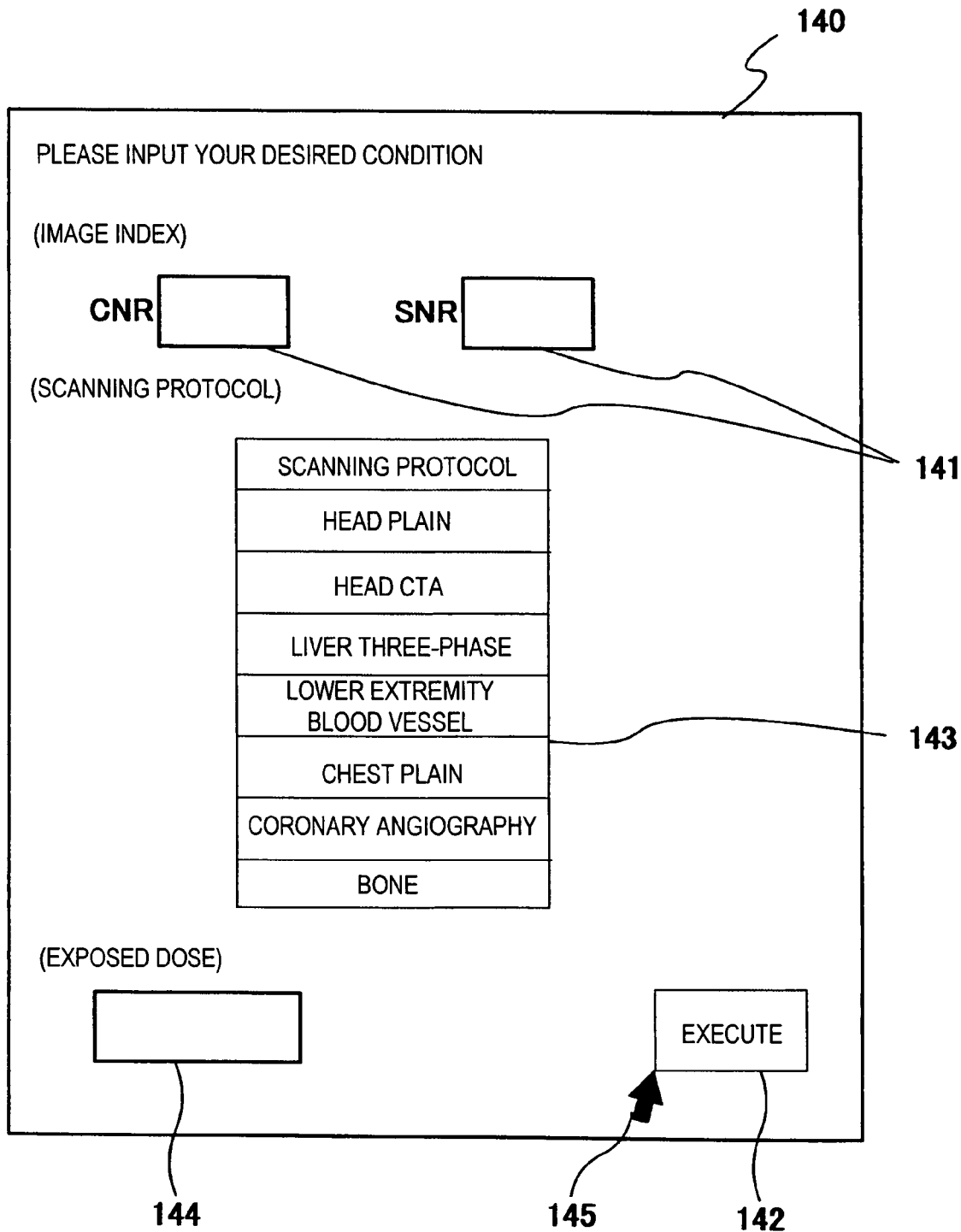
FIG. 12 is a view showing an example of a condition input screen.

FIG. 12 shows an image display example for inputting conditions. A condition input screen 140 includes an index input field 141 for an image quality, an execution button 142, a scanning protocol selection menu 143 and an exposed dose input field 144.

Here, a case is described where the user inputs CNR as the image quality index.

The user inputs a desired value into the input field 141 for CNR or SNR as the image quality index, puts a mouse cursor 145 on the execution button 142 and clicks it. Thereby, a process shown in FIG. 13 is started.

Figure 13:
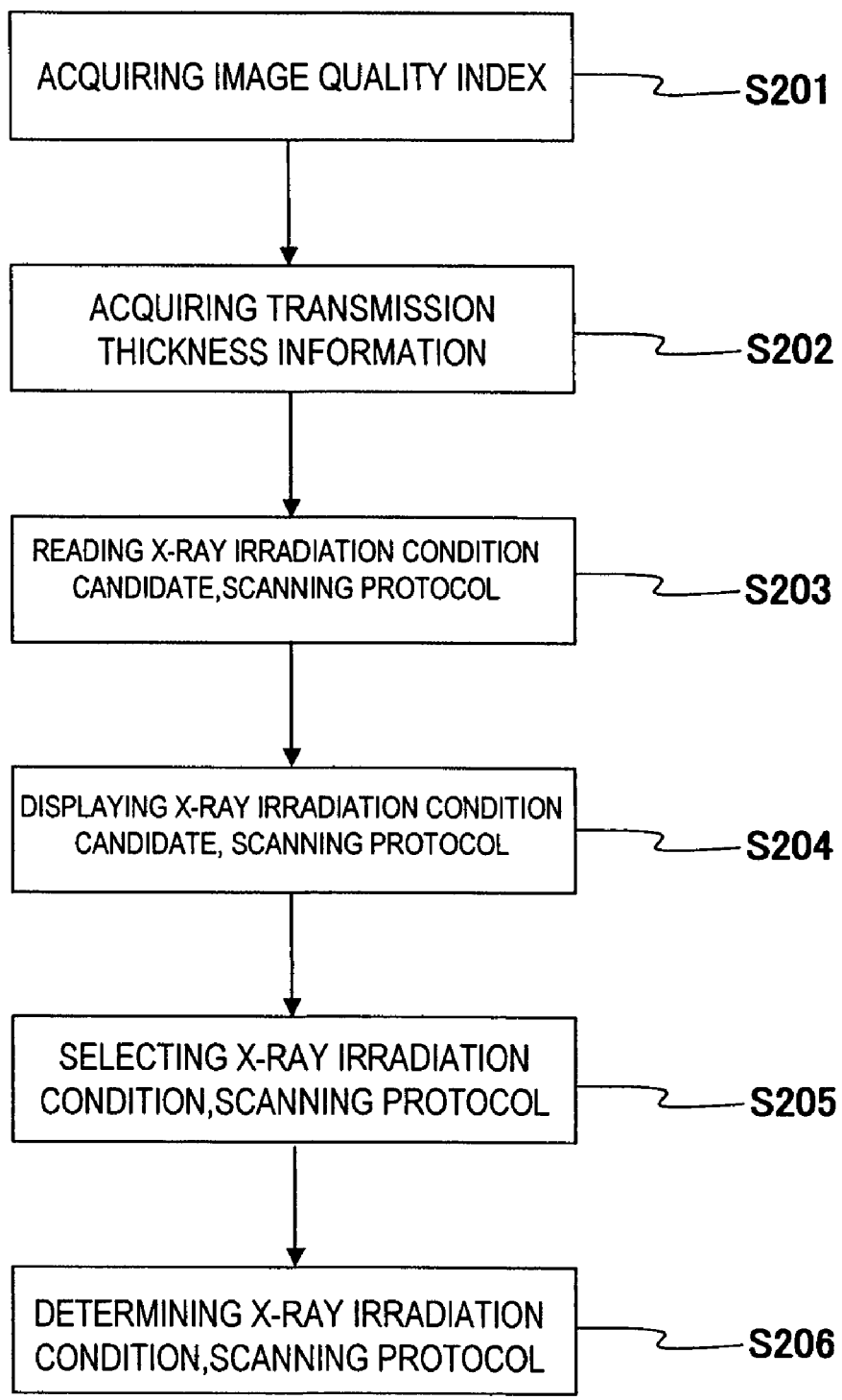
FIG. 13 is a flowchart showing a flow of a process of the second embodiment.

In Step S201, the reading section 20 acquires the inputted CNR information and searches the correlation table of FIG. 13 previously stored in the external storage unit 7. The reading section 20 then reads an X-ray irradiation condition with the closest CNR value.

In Step S202, transmission thickness information is acquired in the same manner as in Step S101.

In Step S203, the reading section 20 reads an X-ray irradiation condition candidate and a scanning protocol, which correspond to the X-ray irradiation condition candidate read in Step S201 and the transmission thickness information acquired in Step S202, from the correlation table of FIG. 11 registered in the external storage unit 7.

In Step S204, the X-ray irradiation condition candidate and scanning protocol read by the reading section 20 in Step S203 is displayed on the display unit 8.

In Steps S205 and S206, an X-ray irradiation condition for use in scanning is selected from the X-ray irradiation condition candidates and then set as in the same manner as Steps S106 and S107.

According to the present embodiment, further preferable X-ray irradiation condition candidates and scanning protocols can be displayed based upon an image quality index value and an object transmission thickness that are desired by the user, and selection can then be made.

Although the image quality index was inputted on the condition input screen 140 of FIG. 12 in the above embodiment, in place of this, the exposed dose may be inputted. Further, a scanning protocol is simultaneously selected on the condition input screen 140 of FIG. 12 by the use of the scanning protocol selection menu 143. Thereby, when extracting X-ray irradiation condition candidates from the correlation table of FIG. 11, the reading section 20 may only refer only to X-ray irradiation condition candidates corresponding to the inputted scanning protocol, thereby allowing improvement in speed of the reference process.

Third Embodiment

In a third embodiment, a scanning protocol is edited and updated for each user, and an X-ray irradiation condition is selected and subjected to a display process based upon a scanning protocol set by the user.

In the present embodiment, a scanning protocol editing section is provided in addition to the components of the X-ray irradiation condition setting 6 according to the first and/or second embodiments.

Figures 14, 15:
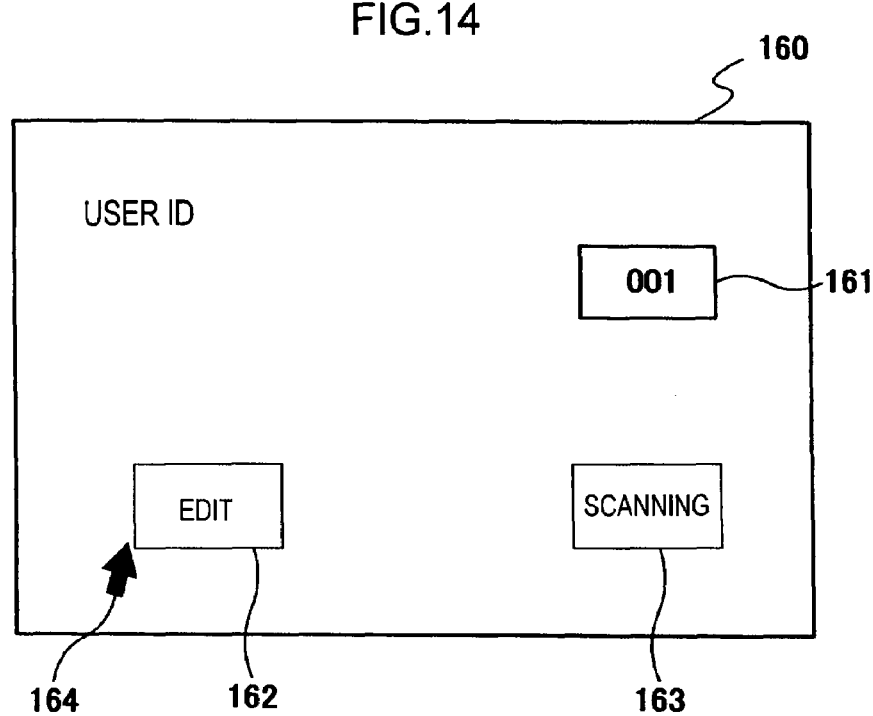
FIG. 14 is a view showing an example of an ID input screen.
FIG. 15 is a view schematically showing a correlation table for use in a third embodiment.

The scanning protocol editing unit displays an ID input screen 160 of FIG. 14. The ID input screen 160 includes a user ID input field 161 for peculiarly identifying the user, an edition button 162 for executing an edition process, and a scanning button 163 for executing a scanning process.

When the user inputs a user ID, puts a mouse cursor 164 on the edition button 162 and clicks it, a scanning protocol/attenuation model table 170 of FIG. 15 is displayed on the display unit 8. In the scanning protocol/attenuation model table 170 of FIG. 15, a user ID record is added to the scanning protocol/attenuation model table of FIG. 2. When the user clicks a record wished to be edited, the display is changed to an edition field 171. The user inputs a desired numeral value into the edition field 171 and clicks a save button 172. Thereby, a user ID can be correlated with a scanning protocol after the edition, which can then be registered into the external storage unit 7. Further, although not shown in the figure, the right mouse button may be clicked to select and display a "row insertion" menu, and a new row may be inserted into the scanning protocol/attenuation model table 170 to set a scanning protocol.

When the scanning button 163 is clicked on the ID input screen 160, the processes of the first and second embodiments are performed based upon the scanning protocol corresponded to the user ID inputted in the ID input field 161.

According to the present embodiment, when scanning protocol is wished to be customized for each user as in a case where each user wishes to see a tissue of different size, it is possible for the user to display and set an X-ray irradiation condition based upon a scanning protocol edited and set by the user.

INDUSTRIAL APPLICABILITY

The present invention allows setting of a further appropriate X-ray irradiation condition mainly based upon a relation of an exposed dose of an object and an image quality, and the present invention is broadly applicable in the field of X-ray CT apparatuses for medical use.

The invention claimed is:

1. An X-ray CT apparatus, comprising:
an X-ray source which irradiates X-rays;
an X-ray detector which is arranged opposite to the X-ray source and detects said irradiated X-rays;
a scanner having a rotary disk which rotatably supports the X-ray source and X-ray detector and a power source of the rotary disk;
an image processing device which makes said scanner rotate in a state where an object is inserted in between said X-ray source and said X-ray detector to irradiate said object with X-rays from directions at a plurality of angles, and makes said X-ray detector detect X-rays transmitted through said object in directions at a plurality of angles as projection data, to reconstruct a tomographic image of said object by use of the projection data in the directions at the plurality of angles;
a display device which displays said reconstructed tomographic image;
a setting device which sets an X-ray irradiation condition including a combination of a tube current and a tube voltage supplied to said X-ray source; and
a control device which supplies said X-ray source with said set X-ray irradiation condition, to perform scanning, wherein
said setting device includes
an X-ray irradiation condition information creating section configured to generate X-ray irradiation condition information, by use of a plurality of X-ray irradiation condition candidates and image quality indexes corresponding to the plurality of X-ray irradiation condition candidates, the image quality indexes being based on a transmission thickness of a scanning subject site of said object and an attenuation model of at least two tissues, and
an X-ray irradiation condition information displaying section configured to cause the X-ray irradiation condition information to be displayed on the display device, for selection of an X-ray irradiation condition candidate from among the plurality of X-ray irradiation condition candidates, the X-ray irradiation condition being set to the selected X-ray irradiation condition candidate.

2. The X-ray CT apparatus according to claim 1, wherein said setting device further includes:
a scanogram analyzing section which analyzes a scanogram of said object to determine the transmission thickness of the scanning subject site of said object; and
an image quality index calculating section configured to calculate an image quality index corresponding to an X-ray irradiation condition candidate from among the plurality of X-ray irradiation condition candidates.

3. The X-ray CT apparatus according to claim 2, wherein said image quality index calculating section calculates the image quality index based on at least one of a contrast/noise ratio and a signal/noise ratio.

4. The X-ray CT apparatus according to claim 2, wherein said image quality index calculating section calculates a contrast/noise ratio, and
said X-ray irradiation condition information creating section calculates an index value obtained by [(the contrast/noise ratio)/the exposed dose], and generates the X-ray irradiation condition information by further correlating said index value with the X-ray irradiation condition candidate.

5. The X-ray CT apparatus according to claim 2, wherein said image quality index calculating section calculates said image quality index, using the attenuation model obtained by modeling tissue configuration in said scanning subject site.

6. The X-ray CT apparatus according to claim 2, wherein said image quality index calculating section calculates said image quality index, using the transmission thickness of said scanning subject site based upon a scanogram image obtained by scanogram imaging.

7. The X-ray CT apparatus according to claim 2, wherein said display section sorts the X-ray irradiation condition information generated by said X-ray irradiation condition information creating section in order of suitability of the image quality indexes or in order of adaptability to a condition designated by the user, and displays the sorted information.

8. The X-ray CT apparatus according to claim 1, wherein
said setting device further comprises an exposed dose calculating section which calculates an exposed dose of said object expected when scanning is carried out with said X-ray irradiation condition candidate set as the X-ray irradiation condition, the exposed dose being calculated based on the transmission thickness of the scanning subject site of said object and an X-ray absorption coefficient of the scanning subject site, and
said control device displays on said display device said calculated exposed dose correlated with said X-ray irradiation condition candidate.

9. The X-ray CT apparatus according to claim 8, wherein said exposed dose calculating section calculates said exposed dose, based on the attenuation model obtained by modeling tissue configuration in said scanning subject site.

10. The X-ray CT apparatus according to claim 8, wherein said exposed dose calculating section calculates said exposed dose by the use of the transmission thickness of said scanning subject site based upon a scanogram image obtained by scanogram imaging.

11. The X-ray CT apparatus according to claim 1, further comprising:
a protocol storage section which correlates a scanning protocol information including at least one of the scanning subject site, a scanning direction and a scanning kind of said object with an X-ray irradiation condition candidate information by at least one piece of combination of a tube current and a tube voltage which corresponds to the scanning protocol information, and stores the correlated information;
a scanning protocol display section which reads said scanning protocol information from said protocol storage section and displays the read information; and
a protocol selecting section which selects said displayed scanning protocol information, wherein
said control device reads a scanning protocol information selected by said protocol selecting section from said protocol storage section, and calculates an X-ray irradiation condition candidate information from the read scanning protocol information.

12. The X-ray CT apparatus according to claim 11, wherein
said setting device further comprises an exposed dose calculating section which calculates an exposed dose of said object expected when scanning is carried out with said X-ray irradiation condition candidate set as the X-ray irradiation condition, the exposed dose being calculated based on the transmission thickness of the scanning subject site of said object and an X-ray absorption coefficient of the scanning subject site, said protocol storage section stores the exposed dose calculated by said exposed dose calculating section, further correlated with said X-ray irradiation condition candidate, said control device further reads the exposed dose corresponding to an inputted image quality index, and said X-ray irradiation condition information display section further displays said read exposed dose.

13. The X-ray CT apparatus according to claim 1, wherein the setting device further includes:

an image quality index calculating section configured to calculate an image quality index for a candidate X-ray irradiation condition, by use of the transmission thickness of the scanning subject site of said object and by applying the candidate X-ray irradiation condition to the attenuation model which models tissue configuration in said scanning subject site and corresponds to a specific scanning protocol.

* * * * *